US011833524B2

United States Patent
Oscarsson et al.

(10) Patent No.: US 11,833,524 B2
(45) Date of Patent: Dec. 5, 2023

(54) COMBINATORY SEPARATION

(71) Applicant: LAB-ON-A-BEAD AB, Gothenburg (SE)

(72) Inventors: Sven Oscarsson, Stockholm (SE); Per-Olof Eriksson, Strängnäs (SE); Kristofer Eriksson, Strängnäs (SE)

(73) Assignee: LAB-ON-A-BEAD AB, Gothenburg (SE)

( * ) Notice: Subject to any disclaimer, the term of this patent is extended or adjusted under 35 U.S.C. 154(b) by 251 days.

(21) Appl. No.: 16/621,908

(22) PCT Filed: Jun. 13, 2018

(86) PCT No.: PCT/EP2018/065643
§ 371 (c)(1),
(2) Date: Dec. 12, 2019

(87) PCT Pub. No.: WO2018/234115
PCT Pub. Date: Dec. 27, 2018

(65) Prior Publication Data
US 2020/0114369 A1  Apr. 16, 2020

(30) Foreign Application Priority Data

Jun. 19, 2017  (SE) .................................. 1750780-7

(51) Int. Cl.
*B03C 1/28* (2006.01)
*B03C 1/30* (2006.01)
(Continued)

(52) U.S. Cl.
CPC .............. *B03C 1/01* (2013.01); *B03C 1/0332* (2013.01); *B03C 1/0335* (2013.01); *B03C 1/288* (2013.01);
(Continued)

(58) Field of Classification Search
None
See application file for complete search history.

(56) References Cited

U.S. PATENT DOCUMENTS 5,536,475 A * 7/1996 Moubayed ............. A61K 35/16
  209/217
2005/0266394 A1* 12/2005 Hatton .................... C12N 1/02
  436/526

(Continued)

FOREIGN PATENT DOCUMENTS

CN  101010592 A  8/2007
CN  202011883 U  10/2011
(Continued)

OTHER PUBLICATIONS

International Search Report dated Jun. 11, 2018 in corresponding International Application No. PCT/EP2018/065643.

*Primary Examiner* — Bradley R Spies
(74) *Attorney, Agent, or Firm* — Renner, Otto, Boisselle & Sklar, LLP

(57) ABSTRACT

There is disclosed a combinatory separation system comprising: a first compartment adapted to handle a mixture with magnetic beads having an affinity for molecules, comprising a magnet to attract the beads, a second compartment adapted to receive said magnetic beads transferred thereto with a flow of liquid, and said at least one second compartment is adapted to elute said at least one type of molecules to be separated from said magnetic beads, said at least one second compartment has an outlet comprising means for retaining said magnetic beads in the at least one second compartment. Advantages include that the process becomes simpler quicker and thereby less expensive, since the method is able to remove cells and particles, separate molecules and perform virus inactivation in fewer steps (Continued)

compared to the prior art. Further the method is able to provide a more concentrated end product.

26 Claims, 8 Drawing Sheets

(51) Int. Cl.
    *G01N 33/543*    (2006.01)
    *G01N 35/00*     (2006.01)
    *B03C 1/01*      (2006.01)
    *B03C 1/033*     (2006.01)

(52) U.S. Cl.
    CPC ......... *B03C 1/30* (2013.01); *G01N 33/54326* (2013.01); *G01N 35/0098* (2013.01); *B03C 2201/18* (2013.01); *B03C 2201/26* (2013.01)

(56) References Cited

U.S. PATENT DOCUMENTS

| | | |
|---|---|---|
| 2009/0206039 A1 | 8/2009 | Rothmann et al. |
| 2009/0220979 A1* | 9/2009 | Davis ................ B03C 1/286 |
| | | 435/308.1 |
| 2011/0223583 A1 | 9/2011 | Gordon et al. |
| 2014/0170652 A1 | 6/2014 | Sitdikov et al. |
| 2016/0184737 A1* | 6/2016 | Oscarsson .......... B01D 15/3885 |
| | | 210/656 |

FOREIGN PATENT DOCUMENTS

| | | |
|---|---|---|
| EP | 2541250 A1 | 1/2013 |
| GB | 2460765 A | 12/2009 |
| WO | 2006/010584 A1 | 2/2006 |
| WO | 2009076560 A2 | 6/2009 |
| WO | 2015/034428 A1 | 3/2015 |

* cited by examiner

COMBINATORY SEPARATION

This application is a national phase of International Application No. PCT/EP2018/065643 filed Jun. 13, 2018 and published in the English language, which claims priority to Swedish Application No. 1750780-7 filed Jun. 19, 2017, both of which are hereby incorporated by reference.

TECHNICAL FIELD

The invention relates to separation of molecules in a mixture comprising several different species. The invention can be used for instance when separating biomolecules in a complex mixture comprising many different dissolved molecules and dispersed solid particles including cells.

BACKGROUND OF THE INVENTION

Since more than 50 years, chromatography has been one of the leading principles for separation of molecules and a vast amount of literature has been published in this area.

One of several important application fields is separation of biomolecules which is today one of the most important areas for industrial separation of molecules from an economical point of view.

Introduction of gel filtration of Porath and Flodin was the starting point for a revolution on research laboratories around the world within life science. Later on several other important inventions such as affinity chromatography and ion exchange chromatography made it possible to make important discoveries within medicine, biology and pharmacy.

Despite the great impact chromatography made on the whole area of life science and biotechnological industries the technique has a few bottlenecks and weak points, which needs to be improved.

One problem is the need of clarification of samples in many cases especially in industrial processes otherwise the risk of clogging is immediately a problem and the backpressure will increase with a direct failure of the process. To avoid that problem all samples need to be processed before applied to the column and it involves e.g. filtering which is a tedious process and involves expensive steps for clarification.

Another problem is the flow rate in the column especially when working with large sample volumes and this is a problem even for a couple of liters of samples. The industrial production of e.g. monoclonal antibodies in the biopharma industry has to handle thousands of liters of sample volumes where the problem is serious.

To avoid the problem with columns, a method based on batch performance during the capturing step could solve several of those problems and to be able to get an effective capturing of biomolecules in solution and an effective washing process to eliminate undesired molecules and fragments and even cells from the solution a batch magnetic separation could be an alternative to traditional chromatography.

One problem with batch magnetic separation has been the low capacity of the magnetic beads to bind biomolecules in affinity chromatographic processes. This problem has been solved by a Swedish company (Lab-on-a-Bead AB) which is now producing magnetic beads with a capacity similar or even higher than corresponding chromatographic media. See for instance EP 2 598 884, EP 2 227 322, EP 3 043 904 U.S. Pat. Nos. 9,389,226, 8,679,807, and 9,777,075.

The problem with the existing technique is that the total volume of the compartment where the beads are captured is large and the volume to elute the biomolecules will consequently be too large and the result will be that the desired biomolecules will be too diluted in its final form.

According to the state of the art when biomolecules from a cell cultures are to be separated and recovered this is done by filtration, separation on columns comprising separation media and subsequent virus inactivation optionally including a separation of the batch in smaller parts before column separation.

WO 2015/034428 discloses process for large-scale separation of molecules comprising mixing magnetic particles with a solution containing molecules to be separated, collecting the magnetic particles molecules, and separating the molecules from the magnetic particles.

WO 2009/111316 discloses a system for separation of molecules from a liquid with magnetic particles. The molecules are eluted in a separate part with smaller volume.

US 2009/0206039 discloses a device for the separation of magnetic particles from a liquid with a first vessel, a second vessel and a connecting surface. The magnetic particles are drawn up from the first vessel over the connecting surface and down to the second vessel.

However although there are existing methods today is a need for a system and a method which is faster, simpler and thereby less expensive. There is a need for a system and method which is able to separate molecules form a mixture, including removal of particles and/or cells as well as virus inactivation and provide the desired molecules in a solution which is sufficiently concentrated for further use.

SUMMARY OF THE INVENTION

It is an object of the invention to alleviate at least some of the problems in the prior art and provide an improved system for the separation of molecules as well as a method thereof.

The inventors have conducted extensive research and found a system and a method, which is able to separate molecules, remove cells and particles, perform virus inactivation and also provide a concentrated end product.

In a first aspect there is provided a system for the separation of molecules in a mixture, said system comprises: at least one first compartment adapted to receive said mixture, and said first compartment is adapted to handle said mixture together with magnetic beads having an affinity for at least one type of molecules to be separated, said system comprises at least one magnet adapted to attract said magnetic beads at least after contact of said mixture with said magnetic beads, said at least one magnet is adapted to exert a magnetic field in at least a part of said first compartment, wherein said system comprises at least one second compartment, said at least one second compartment is adapted to receive said magnetic beads after said magnetic beads have been at least partially collected with said at least one magnet, said at least one second compartment has a volume adapted to receive the volume of said magnetic beads, said system is adapted for transfer of said magnetic beads from said at least one first compartment to said at least one second compartment with a flow of liquid, said at least one second compartment is adapted to elute said at least one type of molecules to be separated from said magnetic beads, said at least one second compartment has an outlet comprising means for retaining said magnetic beads in the at least one second compartment.

In a second aspect there is provided a method for separation of molecules in a mixture, said method comprises the steps of:

contacting the mixture with magnetic beads, said magnetic beads having an affinity for at least one type of molecules to be separated, so that at least a part of the at least one type of molecules to be separated are bound to the magnetic beads, in a first compartment: attracting the magnetic beads with a magnetic field and discarding at least a part of the remaining mixture, optionally washing the magnetic beads under conditions where the at least one type of molecules to be separated are bound to the magnetic beads, transferring the magnetic beads to a second compartment with a liquid, said at least one second compartment having a volume adapted to receive the volume of said magnetic beads, in the second compartment; eluting by adding a liquid to the magnetic beads under conditions so that the at least one type of molecules to be separated are not bound to the magnetic beads, to elute the at least one type of molecules to be separated and collecting the eluate.

Further aspects and embodiments are described in the appended claims.

Advantages of the invention include that the process becomes simpler quicker and thereby less expensive, since the method is able to remove cells and particles, separate molecules and perform virus inactivation in fewer steps compared to the prior art. Further, the method is able to provide a more concentrated end product.

BRIEF DESCRIPTION OF THE DRAWINGS

The invention is described with reference to the following drawings in which.

DETAILED DESCRIPTION

Figure 1:
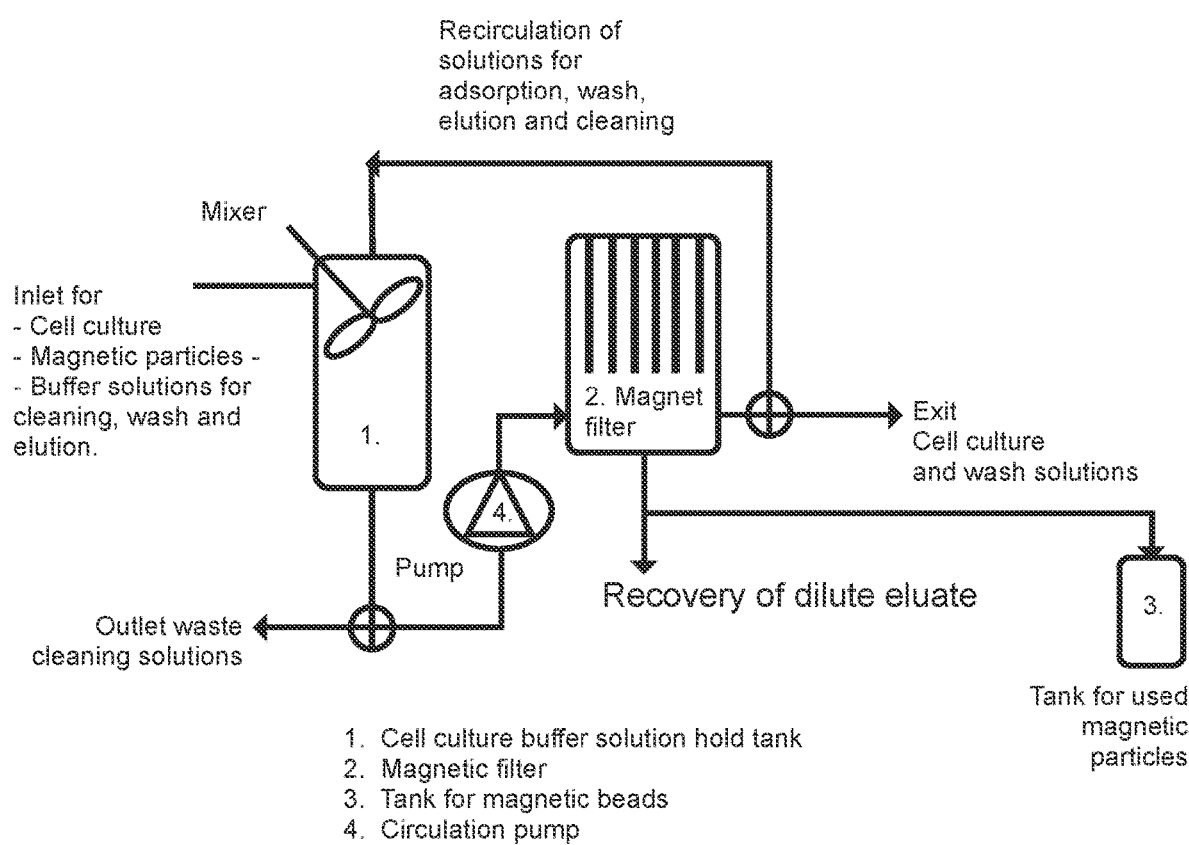
FIG. 1 shows a system according to the state of the art. 1. A mixer to mix cell culture with magnetic beads before entering into the first compartment. 2. The first compartment, also called a magnetic filter. 3. A tank for used magnetic particles. 4. A circulation pump exerting a low shear force on the mixture.
Figure 2:
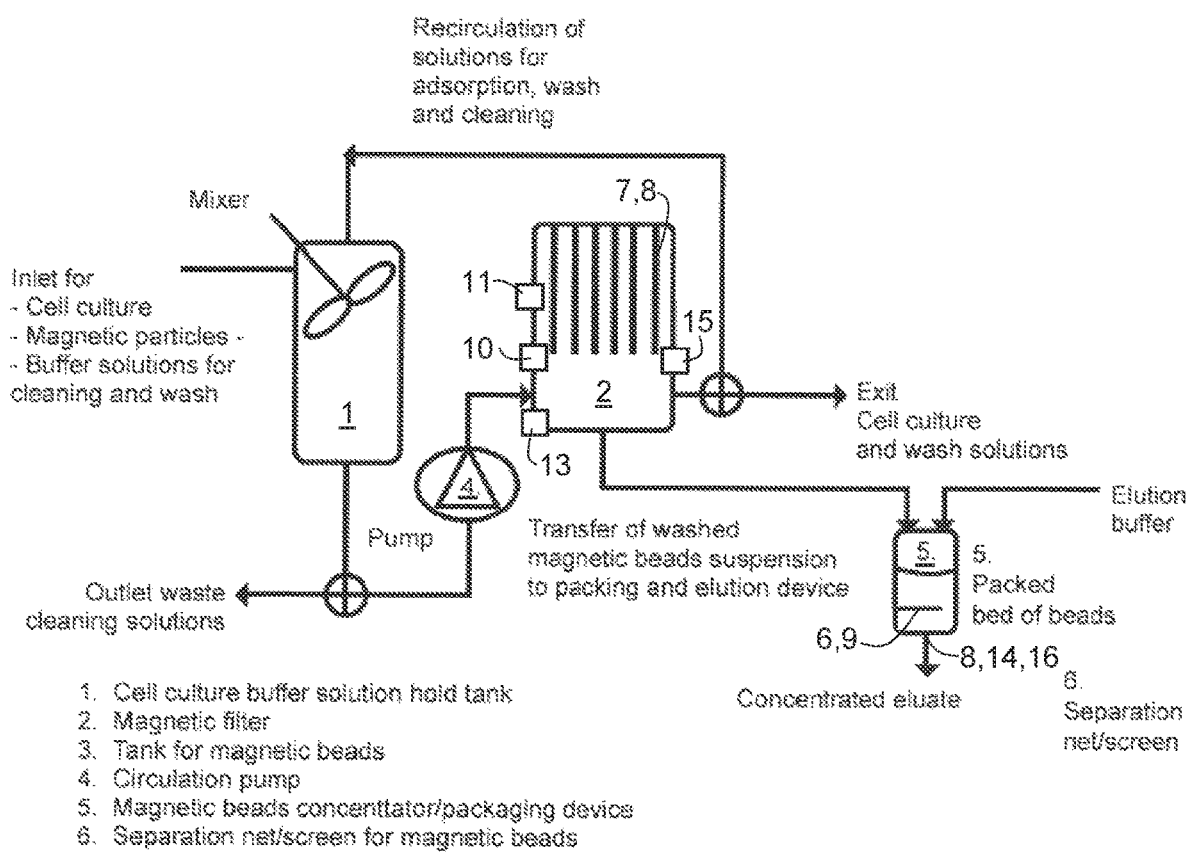
FIG. 2 shows a system according to the present invention. 1. A mixer to mix cell culture with magnetic beads before entering into the first compartment. 2. The first compartment, also called a magnetic filter. 4. A circulation pump exerting a low shear force on the mixture. 5. The second compartment also called a concentrator/packing device. 6. Separation net/screen for magnetic beads to prevent magnetic beads from leaving the second compartment.
Figure 3:
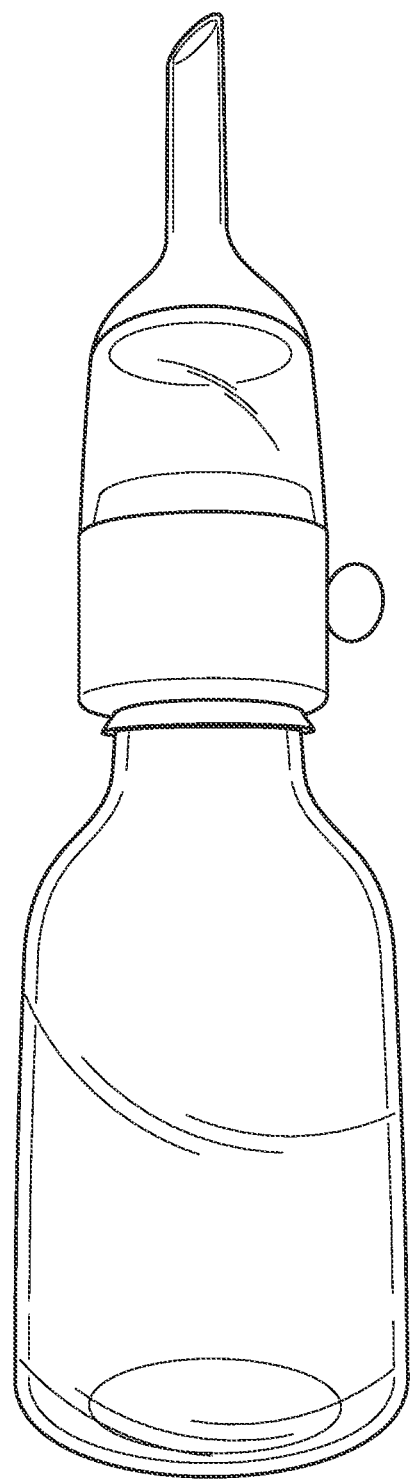
FIG. 3 shows another example for the second compartment (concentrator/packing device) according to the present invention. A device is adapted to be attached to a Duran® flask. The device is equipped with a check valve.
Figure 4:
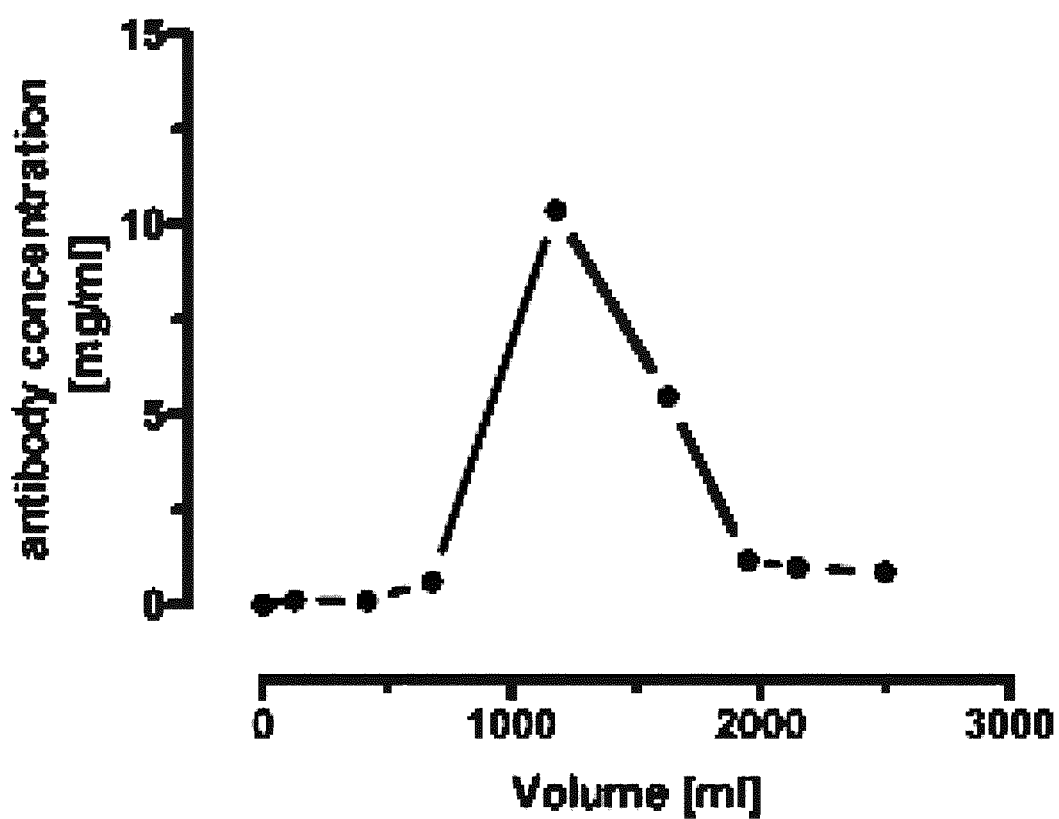
FIG. 4 shows an elution profile as measured by absorbance at 280 nm as detailed in the examples.
Figure 5:
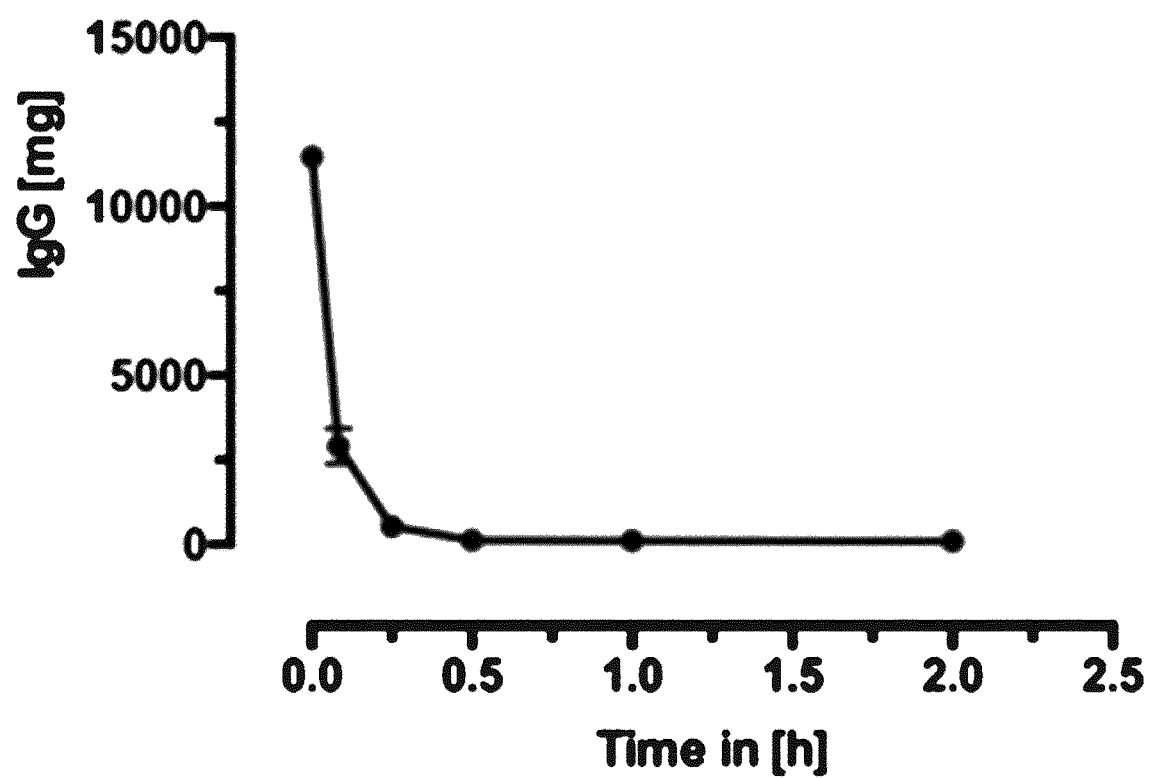
FIG. 5 shows an adsorption profile for mAb to LOABeads MabBind A magnetic beads according to the examples.
Figure 6:
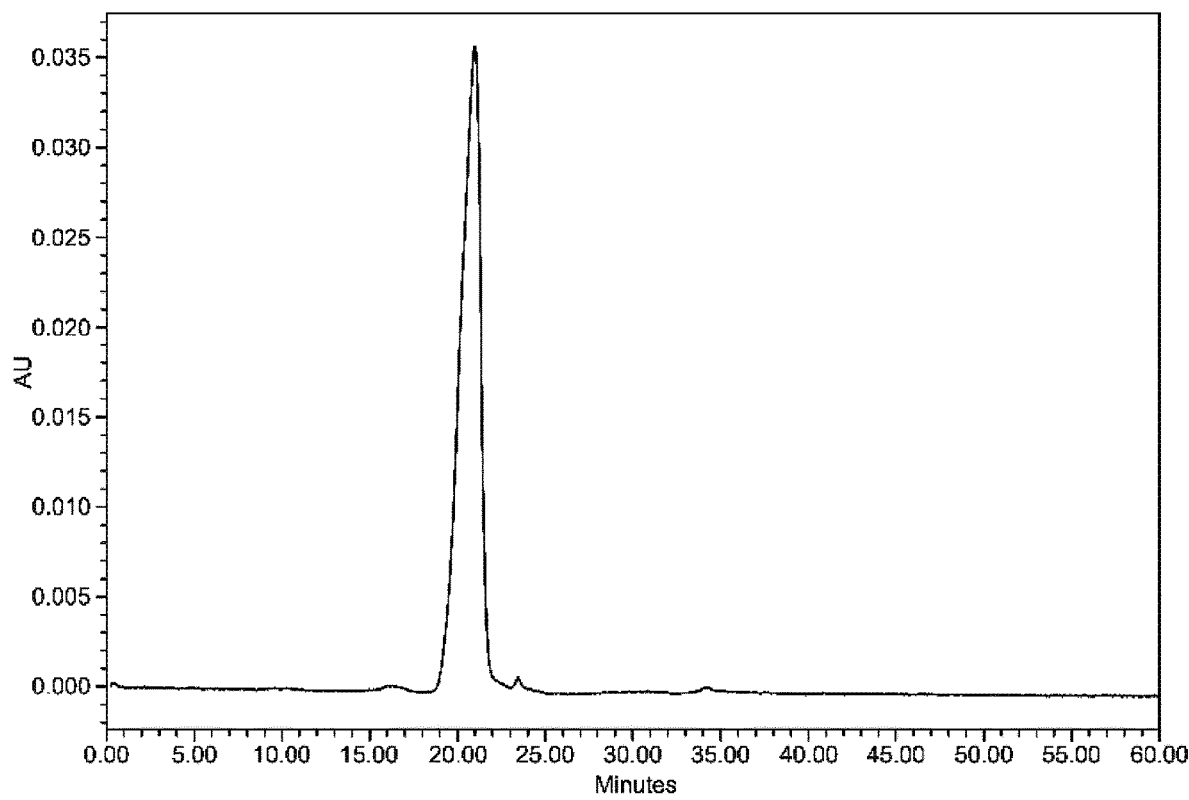
FIG. 6 shows results from samples taken at T0, 15, 30, 60 and 120 minutes that were analyzed for residual content of the mAb by Protein A HPLC. SEC-HPLC chromatogram for purified mAb. Column: TSK 3000 SWXL. Injection volume 20 µl. Mobile phase: 10 mM NaH2PO4 pH 7. Flow rate was 0.3 ml/min. UV detection at 280 nm.
Figure 7:
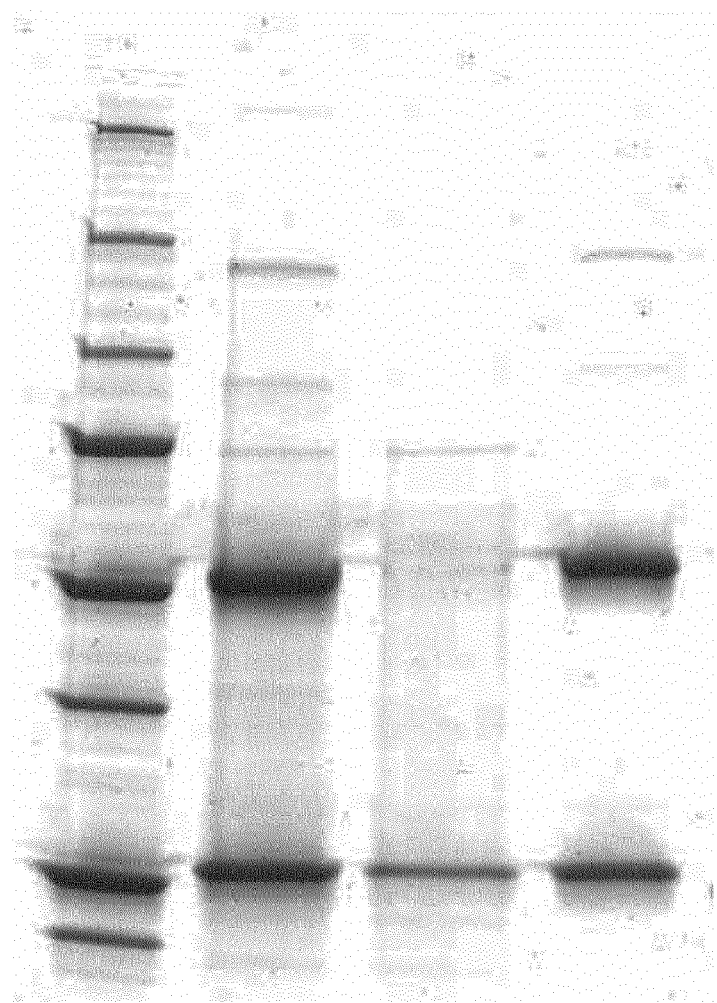
FIG. 7 shows an SDS-PAGE (reduced) gel of un-purified and purified mAb. For SDS-PAGE analysis, protein samples were set to include 1× Laemmli Sample Buffer (BioRad) and 100 mM DTT. Samples were heated to 95° C. for 5 min, cooled to room temperature, where after proteins were separated on a 4-20% Mini-PROTEAN TGX gel (BioRad). Separated proteins were visualized using QC Colloidal Coomassie Stain (BioRad). Lane M, size marker; lane 1, 8 µl input sample; lane 2, 8 µl unbound fraction; and lane 3, 2 µg eluted IgG antibody material.

Before the invention is disclosed and described in detail, it is to be understood that this invention is not limited to particular compounds, configurations, method steps, substrates, and materials disclosed herein as such compounds, configurations, method steps, substrates, and materials may vary somewhat. It is also to be understood that the terminology employed herein is used for the purpose of describing particular embodiments only and is not intended to be limiting since the scope of the present invention is limited only by the appended claims and equivalents thereof.

It must be noted that, as used in this specification and the appended claims, the singular forms "a", "an" and "the" include plural referents unless the context clearly dictates otherwise.

If nothing else is defined, any terms and scientific terminology used herein are intended to have the meanings commonly understood by those of skill in the art to which this invention pertains.

The term "about" as used in connection with a numerical value throughout the description and the claims denotes an interval of accuracy, familiar and acceptable to a person skilled in the art. Said interval is ±10% of the numerical value.

All percentages are calculated by weight unless otherwise clearly indicated.

In a first aspect there is provided a system for the separation of molecules in a mixture, said system comprises: at least one first compartment adapted to receive said mixture, and said first compartment is adapted to handle said mixture together with magnetic beads having an affinity for at least one type of molecules to be separated, said system comprises at least one magnet adapted to attract said magnetic beads at least after contact of said mixture with said magnetic beads, said at least one magnet is adapted to exert a magnetic field in at least a part of said first compartment, wherein said system comprises at least one second compartment, said at least one second compartment is adapted to receive said magnetic beads after said magnetic beads have been at least partially collected with said at least one magnet, said at least one second compartment has a volume adapted to receive the volume of said magnetic beads, said system is adapted for transfer of said magnetic beads from said at least one first compartment to said at least one second compartment with a flow of liquid, said at least one second compartment is adapted to elute said at least one type of molecules to be separated from said magnetic beads, said at least one second compartment has an outlet comprising means for retaining said magnetic beads in the at least one second compartment.

The first compartment in the system is adapted to receive the mixture suitably by having an inlet where the mixture can be added. Suitably there is also a way for air or gas in the first compartment to escape when the mixture is added.

The mixture is a liquid mixture typically comprising dissolved species and optionally dispersed matter.

The magnetic beads are conceived to be a part of the system for the separation of molecules. However the magnetic beads are not inside the system at all times in all embodiments, in some embodiments at least a part of the magnetic beads can be outside the system for at least some time during the operation. The volume of the magnetic beads are adapted to fit into the second compartment. The magnetic beads can be added to the mixture either before it enters to the first compartment or in the first compartment or a combination of before and in the first compartment. The first compartment is adapted to handle the mixture together with the magnetic beads. In one embodiment there is a pump adapted to circulate the mixture and the magnetic beads in the first compartment. In another embodiment there is a stirrer in the first compartment so that the mixture and the magnetic beads are moved around in the first compartment. In one embodiment an orbital shaker is used for mixing and moving fluids and magnetic beads.

The magnetic beads are tailored for the molecules intended to be separated from the mixture. One or several different molecules can be separated from the mixture. The parts of the magnetic beads which are accessible for a liquid are coated with molecules having an affinity for the molecule (s) to be separated. This affinity differs from case to case depending on the molecules. A skilled person can in the light of this description find a suitable system for binding of the molecules to the beads. Examples include but are not limited to antibodies where a suitable antigen is attached to the beads.

The magnetic beads preferably have a fairly high magnetic moment so that they can easily be handled by applying a magnetic field.

The system comprises a second compartment where the magnetic beads are transferred after being collected and separated from the mixture. Suitably, but not always mandatory, the magnetic beads are washed before being transferred to the second compartment. In the second compartment a liquid is added to the beads so that the molecule to be separated from the beads and is retained in the liquid. This process is called elution. The condition for eluting the desired molecules is adapted to the affinity between the molecules to be separated and the magnetic beads. In the example of antibodies it can be a lower pH. Other examples include but are not limited to pH, ionic strength, temperature, addition of other substances etc.

An advantage of transferring the magnetic beads to a second compartment for elution is that the molecules becomes much more concentrated. The volume of the second compartment is typically smaller than the first compartment. The magnetic beads should fit into the second compartment with some margin for additional liquid. The at least one second compartment has a volume adapted to receive the volume of said magnetic beads. The volume of the second compartment should be a bit larger than the volume of the magnetic beads so that the magnetic beads can fit into the second compartment and so that a liquid for elution of the relevant molecules can be added. The volume of the second compartment should however not be too large, because then the molecules to be eluted become too dilute. In one embodiment, the volume of the at least one second compartment is less than three times the volume of the magnetic beads intended to be used in the system to allow a generous margin for liquids. In one embodiment, the volume of the at least one second compartment is less than twice the volume of the magnetic beads intended to be used in the system to allow a margin for liquids. In another embodiment the volume of the at least one second compartment is not more than 150% of the volume of the magnetic beads. In yet another embodiment the volume of the at least one second compartment is not more than 120% of the volume of the magnetic beads. In yet another embodiment the volume of the at least one second compartment is not more than 110% of the volume of the magnetic beads. The volume of the beads is measured by pouring the beads into a measurement volume and letting any liquid drip off by gravity until no more liquid comes out from the magnetic beads. In one embodiment, the volume of the at least one second compartment is 5% of the volume of the at least one first compartment. In one embodiment, the volume of the at least one second compartment is 10% of the volume of the at least one first compartment. In one embodiment, the volume of the at least one second compartment is 20% of the volume of the at least one first compartment.

In one embodiment, the amount of eluting buffer is adapted to the volume of magnetic particles. The amount of eluting buffer should not be too large in relation to the volume of magnetic beads in order to obtain a good concentration of molecules. In one embodiment, the volume of the eluting buffer is less than four times the volume of the magnetic beads. In another embodiment the volume of the eluting buffer is less than three times the volume of the magnetic beads. In yet another embodiment the volume of the eluting buffer is less than twice the volume of the magnetic beads. In one embodiment, the volume of the liquid added to elute in step e) is less than four times the volume of the magnetic beads in the second compartment.

In one embodiment, the system comprises means for removing liquid form the beads in the second compartment before the elution starts. This means is typically means for applying a suction and an air or gas inlet. Thus the concentration of the end product can be increased further.

The second compartment is adapted to elute the molecules to be separated by having an inlet for the elution liquid and an outlet for elution liquid. There should also be means retaining the magnetic particles in the second compartment, for instance a net, a filter or similar.

In one embodiment said at least one magnet is at least one selected from the group consisting of a permanent magnet, and an electromagnet.

In one embodiment said at least one magnet is shaped as at least one retractable rod, said at least one retractable rod is positioned at the first compartment so that it can be inserted into and retracted from the first compartment.

In one embodiment said at least one magnet can be inserted and retracted inside at least one sheath in the first compartment. Thereby the at least one sheath is permanently inside the at least one first compartment, whereas the magnet (s) are inserted and retracted inside the sheath(s) to control the magnetic field.

The system is adapted for transfer of said magnetic beads from said at least one first compartment to said at least one second compartment with a flow of liquid. It is intended that there is a flow of liquid, which brings the magnetic particles from the first compartment to the second compartment. When the magnetic particles have been collected in the first compartment using the magnet, a flow of liquid is used to transport the magnetic particles to the second compartment. The magnetic force can be reduced by removing or retracting a permanent magnet or switching off an electromagnet when the flow of liquid transports the magnetic particles to the second compartment. In one embodiment, the second compartment is located under the first compartment to facilitate flushing the magnetic particles down to the second compartment. In one embodiment, the second compartment has a drain so that the magnetic particles remain but the liquid used for the transport flows away from the second compartment.

In one embodiment, the first compartment comprises at least one nozzle adapted for directing a liquid at least partially towards a position where magnetic beads gather after being attracted by said at least one magnet. It is conceived that the magnetic particles are collected by magnetic force and the remaining liquid is removed from the first compartment through an outlet. When the magnetic particles are to be transferred further a flow of liquid is utilized to bring the particles to the desired position. For instance liquid is preferably pumped towards the position(s) where the magnetic field has collected the magnetic beads. If the magnetic field can be controlled the magnetic field is preferably weakened or turned off when the magnetic beads are to be removed from the magnetic field and transferred away.

In one embodiment where there is at least one sheath or rods inside the first compartment, one nozzle directs a liquid at least partially towards the outside of said at least one sheath. If there are several sheaths liquid is sprayed onto the sheaths or rods so that the magnetic particles are transferred away and follows the flow of the liquid. The liquid sprayed towards the particles create a flow of liquid which brings the particles with the flow.

A liquid to be utilized for removing the magnetic beads from the first compartment should be such that the molecules to be separated still is bound to the magnetic beads. According to the invention the elution should be performed in the second compartment.

In one embodiment, the second compartment is located below the first compartment so that the magnetic beads can be flushed down from the first compartment to the second compartment.

In one embodiment, the system comprises pump(s) exerting low shear force on a pumped liquid. In one embodiment, the system comprises a peristaltic pump(s). Since the system in many cases should be able to handle cells, it is suitable that the entire system is designed so that cells are not ruptured by shear force. Such an adaption can easily be made by using pumps exerting low shear force and by using moderate pressure and flow velocity of the liquids. In one embodiment, the system is adapted to handling cells.

In one embodiment, the system is connected to a process computer system. Thereby the process can be automated, either fully or at least partially.

In one embodiment at least one from analogue and digital sensors are connected to a process computer system. The sensors will help to determine how the system should be operated.

In one embodiment said system comprises at least one level sensor. Level sensors are known for a person skilled in the art will help to determine the state of the separation process. In one embodiment an UV-detector is at an exit of said at least one second compartment. In one embodiment a detector capable of measuring the optical density of a fluid is in said at least one first compartment. In one embodiment said detector measures the optical density using light with a wavelength in the interval 400-600 nm.

In one embodiment, the computer system is connected to the user's right to use the system. For instance In one embodiment, the computer system is connected remotely to a server, where the server determines if the user can use the system or not. The determination of the allowed use of the system can be made according to payments from the user.

In one embodiment at least one selected from the group consisting of a net and a filter is positioned at an exit of the second compartment, and which has a size of through pores so that it has the ability of retaining the magnetic beads in the second compartment. The second compartment of the system has an outlet comprising means for retaining said magnetic beads in the at least one second compartment. This means to retain the magnetic beads is suitably some kind of net or filter with a suitable dimension adapted so that the magnetic beads do not pass the net or filter, but so that liquid can pass.

In one embodiment a sterile filter is at an exit of the second compartment. A sterile filtration suitably together with a virus inactivation at low pH would provide a fast and attractive way of obtaining a sterile end product ready for further use.

In one embodiment, the second compartment is a storage for magnetic beads, when the system is not in use. After the elution of the molecule to be separated the magnetic beads can be washed in the second compartment and a bacteriostatic agent can be added. Then the magnetic beads can be stored in the second compartment until next use. Typically, the magnetic beads can be used multiple times, although it is possible to use the magnetic beads only once and thereafter discard them.

In one embodiment, the second compartment is detachable and sealable. Thereby the second compartment can be removed and stored elsewhere. When the next run is to be made, this facilitates the addition of the magnetic beads in the process.

In one embodiment, the at least one first compartment is a flask, and wherein the at least one second compartment is a container attached on said flask and in fluid connection with said flask, wherein the system is adapted to be turned upside down when magnetic particles are to be transferred to the second compartment, and wherein the second compartment comprises at least one selected from a net and a filter positioned at an exit of the second compartment, and which has a size of through pores so that it has the ability of retaining the magnetic beads in the second compartment.

This is a simple and small-scale version of the system suitable for small scale separation. A standard laboratory flask with a standard screw cap is in one embodiment utilized. The second compartment comprising inlet and outlet as well as a net or a filter is then screwed onto the flask before the magnetic particles are transferred to the second compartment. The magnetic beads are collected in the first compartment by using a magnet from outside the flask. In one embodiment, the system is mounted in a holder, which can be rotated from a first position where the first compartment is downwards to a second position where the second compartment is downwards. In one embodiment, the system comprises an inlet comprising a check valve. In one embodiment, the check valve has a vent filter preventing contamination of the contents of the system. The vent filter prevents contaminants in the surroundings to enter into the system.

In one embodiment, the system is intended for single use to be discarded after use. This is typically envisaged for a small-scale system.

In one embodiment parts of the system intended to be in contact with the mixture are intended for single use to be discarded after use and where other parts of the system are intended for use more than once. Examples of parts intended to be in contact with the mixture include but are not limited to the inside of the first and second compartments as well as tubes.

In one embodiment, the system is washable. In one embodiment, the system is autoclavable. In one embodiment, the system meets pharma engineering standards. This means in practice that the system is made of for instance polished stainless steel of pharmaceutical grade or other material of pharmaceutical grade. There are several different standards covering process control, design, and performance, as well as quality acceptance/assurance tests for the pharmaceutical manufacturing industry. One example is ASTM E2500-13 "Standard Guide for Specification, Design, and Verification of Pharmaceutical and Biopharmaceutical Manufacturing Systems and Equipment".

In one embodiment the system comprises at least two first compartments in series. In an alternative embodiment the system comprises at least two first compartments in parallel. Thus, there can be several first compartments and they can be connected in series or in parallel or in any combination thereof. A mixture to be purified is thus pumped through the first compartments. For instance it may be more scalable to connect several smaller units as first compartments.

In one embodiment the system comprises at least two second compartments in parallel. Thus there can be several second compartments in parallel.

In one embodiment the system comprises at least one magnet adapted to attract said magnetic beads by exerting a magnetic field in at least a part of said second compartment. Such a magnet(s) can be an electromagnet and/or a permanent magnet. Such a magnet in the second compartment can facilitate the concentration and packing of beads in the second compartment before the elution. Thus when used the magnetic beads are attracted by at least one magnet in the second compartment. The magnetic beads are first collected with the magnet in the first compartment and then moved to the second compartment with the aid of a flowing liquid. The magnetic beads are in this embodiment attracted by a magnetic field in the second compartment.

In a second aspect there is provided a method for separation of molecules in a mixture, said method comprises the steps of:

contacting the mixture with magnetic beads, said magnetic beads having an affinity for at least one type of molecules to be separated, so that at least a part of the at least one type of molecules to be separated are bound to the magnetic beads, in a first compartment: attracting the magnetic beads with a magnetic field and discarding at least a part of the remaining mixture, optionally washing the magnetic beads under conditions where the at least one type of molecules to be separated are bound to the magnetic beads, transferring the magnetic beads to a second compartment with a liquid, said at least one second compartment having a volume adapted to receive the volume of said magnetic beads, in the second compartment; eluting by adding a liquid to the magnetic beads under conditions so that the at least one type of molecules to be separated are not bound to the magnetic beads, to elute the at least one type of molecules to be separated and collecting the eluate.

In one embodiment step a) is carried out in the first compartment. Then the mixture is added to the first compartment and the magnetic beads are contacted with the mixture in the first compartment.

In an alternative embodiment step a) is carried out before the mixture enters into the first compartment. Then the magnetic particles are contacted with the mixture before the mixture and the particles enter into the first compartment. In one embodiment, the magnetic particles are added in a cell culture before it is fed to the first compartment.

In one embodiment, the conditions under which the at least one type of molecules to be separated are eluted from the magnetic beads is low pH in the interval 2-4.5, preferably 3-3.5, where a simultaneous virus inactivation occurs. Low pH is suitable used when antibodies are to be separated. A low pH has the advantage of providing a virus inactivation so that two steps are performed simultaneous.

In one embodiment, the mixture is pumped into the magnetic field in the first compartment once. This is a single pass mode where the mixture with the magnetic particles passes the magnetic field once. Then the amount of magnetic beads and the strength of the magnetic field as well as the flow rate should be adapted so that most of the magnetic beads are retained in the magnetic field.

In an alternative embodiment the mixture is circulated and pumped into the magnetic field in the first compartment more than once. The mixture including the magnetic field can either be stirred around inside the first compartment where they are retained in a part of the first compartment where there is a sufficiently strong magnetic field, or the mixture including the magnetic particles can be pumped around in a circuit which is partially outside the first compartment with a pump and tubes outside the first compartment. The circulation time can then be adapted so that a sufficient fraction of magnetic beads are retained in the magnetic field in the first compartment.

In one embodiment, the optional washing of the magnetic beads in step c) comprises attracting the magnetic beads with the magnetic field and washing where after the magnetic beads are released from the magnetic field and subsequently attracted with the magnetic field again where after washing is performed again. The magnetic beads are thus first washed when bound to the magnet and then released and bound where after they are washed again. Thus the magnetic beads will be rearranged between the washes. This release and wash can be repeated more than once. The particles closest to a surface will with a high probability obtain a new position further away from the surface and closer to the washing liquid. It is assumed that the washing is least efficient for the magnetic beads closest to the magnet and most efficient for the magnetic beads closest to the washing liquid. It is thereby assumed that much of the transport of molecules will be by diffusion.

In one embodiment remaining liquid is removed with suction before eluting in step e), to further increase the concentration of the at least one type of molecules to be separated. This method step has the advantage of further increasing the concentration by removing liquid.

In one embodiment, the attracting of the magnetic beads with the magnetic field in step b) is monitored by measuring the optical density of the mixture and taking a lower optical density as an increased attraction of magnetic beads in the magnetic field. As the magnetic beads are retained in the magnetic field the optical density of the mixture will decrease since the presence of magnetic particles will increase the optical density. It is envisaged that the retention of magnetic beads is monitored by measuring the optical density both for single pass mode and for circulation mode.

The magnetic beads are transferred to the second compartment with a liquid. The flow of liquid brings the magnetic particles with the liquid and thus transports the magnetic particles. In one embodiment, the magnetic beads are removed from the first compartment by spraying a liquid onto the magnetic particles. Such liquid should be so that the molecules to be separated still are bound to the magnetic beads. The flow of liquid will transfer the magnetic beads to the second compartment. The magnetic particles follow the flow of liquid and are brought with the liquid by the flow. In one embodiment, the magnetic field in the first compartment is decreased or removed before transferring the magnetic beads to the second compartment. The transfer of the magnetic beads is facilitated by reducing or removing the magnetic field.

In one embodiment, the eluting in step e) is monitored by measuring the absorbance at selected wavelength(s) adapted to the at least one type of molecules to be separated and taking an absorbance lower than a threshold value as an indication that a sufficient fraction of the at least one type of molecules to be separated have been eluted. During the elution the concentration of the molecule to be separated is monitored by measuring the absorbance at wavelength(s) adapted to the specific molecule. For proteins including antibodies the UV-absorbance for instance at 280 nm (UV) can be taken as a measure of the concentration.

In one embodiment, the mixture comprises cells. The system and the method is suitable for handling mixtures originating from cell cultures where the cells remain in the mixture when the process starts. The cells can easily be separated and removed together with all other unwanted matter. In one embodiment, the mixture is added from a fed batch culture. In an alternative embodiment the mixture is added from a perfusion culture.

In one embodiment a cleaning is performed after finishing the separation. In one embodiment, the cleaning is performed with a liquid comprising 0.5 M NaOH. This is a standard procedure within many application areas.

In one embodiment good manufacturing practice GMP is followed during the method. GMP may vary between different countries and are guidelines to provide guidance for manufacturing, testing, and quality assurance in order to ensure that a food or drug product is safe for human consumption. The good manufacturing practice is described in detail in "Current Good Manufacturing Practice (CGMP) Regulations" by FDA, the US Food and Drug Administration. These guidelines are generally accepted and are in this application and claims taken as a description of good manufacturing practice.

In one embodiment, the second compartment serves as a storage compartment for magnetic beads after finishing the process and wherein at least one bacteriostatic compound is added to the magnetic beads in the storage compartment. In one embodiment, the bacteriostatic compound is ethanol. A person skilled in the art can select a suitable bacteriostatic compound and can also select a suitable concentration of such a compound to prevent bacteria from reproducing.

In one embodiment, the at least one first compartment is a flask, and wherein the at least one second compartment is a container attached on said flask and in fluid connection with said flask, wherein the system is adapted to be turned upside down when magnetic particles are to be transferred to the second compartment, and wherein the second compartment comprises at least one selected from a net and a filter positioned at an exit of the second compartment, and which has a size of through pores so that it has the ability of retaining the magnetic beads in the second compartment.

In one embodiment a system is used wherein the at least one first compartment is a flask, and wherein the at least one second compartment is a container attached on said flask and in fluid connection with said flask, wherein the system is adapted to be turned upside down when magnetic particles are to be transferred to the second compartment, and wherein the second compartment comprises at least one selected from a net and a filter positioned at an exit of the second compartment, and which has a size of through pores so that it has the ability of retaining the magnetic beads in the second compartment. In this system the second compartment has a volume which is not more than twice the volume of the magnetic beads.

In one embodiment, the eluting in step e) is performed by using pressurized gas. In one embodiment, the eluting in step e) is finalized with a vacuum evacuating the liquid (eluting buffer) from the second compartment. This has the advantage of further reducing the volume of liquid (eluting buffer) and thereby concentrating the sample further.

In one embodiment, the eluting in step e) is performed for a certain period of time before the eluate is collected. Typically the liquid (eluting buffer) is added and after a certain contact time a vent in the second compartment, typically at the bottom is opened so that the eluting buffer can be collected. A filter prevents the magnetic particles from following the liquid and keeps the magnetic particles in the second compartment.

EXAMPLES

Example 1

Procedure for Purifying a Monoclonal Antibody by the Use of the Combinatory Filter 1. Preparation of Cell-Free Harvest Containing a Monoclonal Antibody The harvest was collected in a harvest tank from a perfusion culture of mammalian cells. These cells had been modified using recombinant technology to excrete a monoclonal antibody. The perfusion culture was performed in a bioreactor in which spent medium was continuously removed, so called 'harvested', while fresh culture medium was continuously added at the same flow rate as the harvest was removed from the bioreactor. The harvest was free of cells thanks to a filter installed in the harvest line before the harvest tank. The antibody concentration was determined by Protein A-HPLC and was 0.44 g/L. The volume was 26 liters.

2. Equilibration of LOABeads MabBind a Magnetic Beads, Product Code 1004.

The magnetic beads were equilibrated on a filter funnel (por 2) by 3 bead volumes of PBS buffer. The beads were thereafter resuspended in 2 L of PBS buffer.

3. Adsorption of Monoclonal Antibody to the Magnetic Beads

The suspension of beads was slowly poured into a vessel containing the perfusion culture solution and moderate/sufficient stirring was started. Samples were taken out at time 0, 15, 30, 60 and 120 minutes to follow the kinetics of the adsorption phase by Protein A-HPLC analysis. A greater than 95% adsorption was found after 30 minutes and greater than 99% after 120 minutes. SDS-PAGE analysis showed no residual antibody after 120 minutes.

4. Preparing of the Combinatory Magnetic Filter for Use.

The filter was assembled and connected to a peristaltic pump for pumping of buffers and beads and nitrogen gas for purging purposes. Compressed air was connected for operating the retractable magnets. The system was thoroughly cleaned and drained from PBS buffer. A membrane filter/bead retainer was mounted at the bottom of the second compartment. Next was the upper chamber (first compartment) (volume 7.5 L) filled with PBS buffer by the peristaltic pump.

5. Binding of Magnetisable Beads to the Magnetic Rods of the Upper Chamber Filter (Magnets in the First Compartment).

The superparamagnetic rods (8) were lowered into position into surrounding stainless steel tubes and the magnetic filter was thereby activated. Next was the suspension of perfusion culture and beads pumped into the upper chamber (first compartment) from the bottom. A top valve was opened to allow liquid to exit from the chamber. Samples were continuously taken out to check for any escaping black beads. The flow rate was kept between 100 and 260 L/h until all suspension had been pumped through the chamber (total time 1 hour and 20 minutes). No beads could be found in the liquid pool collected of the effluent.

6. Washing of Unbound Cell Culture Media Components and Impurity Proteins with Beads Bound to the Magnets.

Next were 2 chamber volumes of PBS buffer pumped through the upper chamber to displace cell culture components and impurity proteins. The time elapsed for this step was 15 minutes.

7. First Wash of Re-Suspended Beads with PBS.

One chamber volume of PBS buffer was now pumped through the chamber to displace the previous wash liquid.

Next were the magnetic rods retracted to enable re-suspension of the beads. The PBS buffer from the chamber was now circulated in a loop to enable fast re-suspension of the beads. Flow rate was 290 L/h, time elapsed to obtain resuspension of all beads, 20 minutes. Circulation of the suspension continued for another 15 minutes at 100 L/h, now with the magnets in the activated position, the beads were now attracted to the magnetic rods and the wash liquid was cleared from beads.

8. Second Wash of Re-Suspended Beads with PBS.

One chamber volume of PBS buffer was now pumped through the chamber to displace the previous wash liquid.

Next were the magnetic rods retracted to enable re-suspension of the beads. The PBS buffer from the chamber (first compartment) was now circulated in a loop to enable fast re-suspension of the beads. Flow rate was 290 L/h, time elapsed to obtain resuspension of all beads, 20 minutes. Circulation of the suspension continued for another 15 minutes at 100 L/h, now with the magnets in the activated position, the beads were now attracted to the magnetic rods and the wash liquid was cleared from beads. The wash liquid was drained through the bottom valve of the upper chamber.

9. Third Wash of Re-Suspended Beads and Transfer to Lower Compartment (Second Compartment). The Volume of the Lower Compartment (Second Compartment) was 3 Liters.

One chamber volume of PBS buffer was now pumped into the upper chamber. The wash buffer was now circulated with inactivated magnets through the compartment to enable re-suspension of the washed beads. Next was the bottom valve of the upper and the lower compartment opened simultaneously. The suspension was now cleared from the upper compartment and liquid from the lower compartment (second compartment).

10. Rinse of Upper Compartment (First Compartment) from Beads by Spraying with PBS Buffer.

The upper compartment was now sprayed with 2×2 L of PBS via spray nozzles positioned on both sides of the stainless steel tubes in the chamber, this to recover any residual magnetic beads in the lower compartment (second compartment).

11. Packing of Beads into a Column Bed (in the Second Compartment).

A nitrogen gas pressure was now applied from the upper chamber, the pressure was regulated at 1.5-2 bars. The PBS buffer was drained of through the bottom valve of the lower compartment until about 2-3 cm of liquid remained above the bed surface. The bottom valve of the lower compartment was then closed. The height of the formed column bed was about 13 cm. The volume of the magnetic beads was 1 liter.

12. Desorption, Elution of Monoclonal Antibodies from the Magnetic Beads.

The lower compartment above the formed bed was now filled with elution buffer consisting of 60 mM sodium citrate, pH 3.0 buffer. A nitrogen pressure was again applied, the pressure was kept at 1.5-2 bars. Then the bottom valve was opened slowly to regulate the flow rate of eluate from the chamber. The flow rate was 39 L/h. Fraction were taken of which the absorbance at 280 nm was measured, this to determine when to start and stop collecting the eluate containing the antibodies. The eluate pool collected during 30 minutes had a volume of 2.6 L corresponding to 2 bed volumes and concentrating factor of 10 calculated from the perfusion starting solution. The starting material was 26 liters. The concentration of antibodies in the pool was 3.9 g/L determined by Protein A-HPLC and measurement of A280 nm absorbance. The corresponding yield calculated from the starting solution was 87%.

13. Viral Inactivation by Low pH Treatment Followed by pH Neutralization of the Eluate.

The eluate was gently stirred for 60 minutes which represents a suitable time for efficient viral inactivation. A 2 M Tris buffer pH 9, volume 0.26 L, was then added to increase the pH to 7.4.

14. Regeneration, Cleaning and Sanitation of the Mab-Bind Beads. Cleaning of the Magnetic Filter.

The beads were cleaned with passing 2 bed volumes of elution buffer, followed by 2 volumes of 60 mM citrate pH 2.3 buffer and 3 bed volumes of PBS buffer and finally by 3 bed volumes of PBS buffer containing 20% ethanol as a preservative. The beads were thereafter stored as a 25% suspension at 2-8° C. before next use.

15. Qualitative Evaluation of the Purified Monoclonal Antibody.

Analysis was performed by SEC-HPLC. One main peak representing the monomer antibody was noticeable in the chromatogram. The SDS-PAGE under reduced conditions analysis showed two main bands, the light and heavy chain of the antibody.

Example 2. Medium-Scale Purification of Human IgG Antibodies by the Use of Combinatory Magnetic Separation and Filtration 1. Purpose Antibody purification with Protein A coupled magnetic beads using magnetic separation is convenient with low-tech and low-cost instruments compare to traditional column chromatography. A possible drawback is the elution volume when separating beads from desorbed antibodies using the magnetic separation. Typically, 2× 10 bead volumes is used to reach high yields and utilize the full separation strength of the magnets.

In comparison, column chromatography is typically that over 90% of the desorbed antibodies are found in 3 column volumes of elution buffer.

Here we investigate the possibility to drastically decrease the elution volume found in magnetic separation by using a combinatory magnetic separation and filtration approach.

2. Method 100 ml 10% slurry of Protein A coupled LOABeads™ was transferred to a 500 ml Duran bottle (first compartment).

400 ml of phosphate buffered saline (PBS) was added and the suspension was manually mixed for 30 seconds before separation in a LOABeads MagSep 500 separator.

After approximately 5 minutes the magnetic beads were attracted to the magnets and the liquid was removed by pipetting.

The beads were re-suspended in 480 ml of PBS.

20 ml of human serum (Input) was added and the solution was mixed using an orbital shaker (200 rpm).

After 2 hours binding the unbound was collected using magnetic separation (LOABeads MagSep 500).

The beads were washed with 3× 500 ml of PBS using magnetic separation.

Beads were re-suspended in additional 500 ml PBS and the Topfilter (second compartment) was mounted and the Duran bottle was placed up-side down on a suction flask.

PBS solution was removed using a water suction device.

Topfilter was de-mounted from the Duran bottle.

The bound IgG antibodies were eluted by addition of 6× 10 ml citric acid (60 mM, pH 3.0) to the beads when present on the filter.

IgG antibodies were allowed to desorb from beads for 1 minute before flushing through the filter.

The 6× elution fractions were further filtered (0.4 μm) and kept for protein content analysis.

3. Analysis of Elution Fractions

Figure 8:
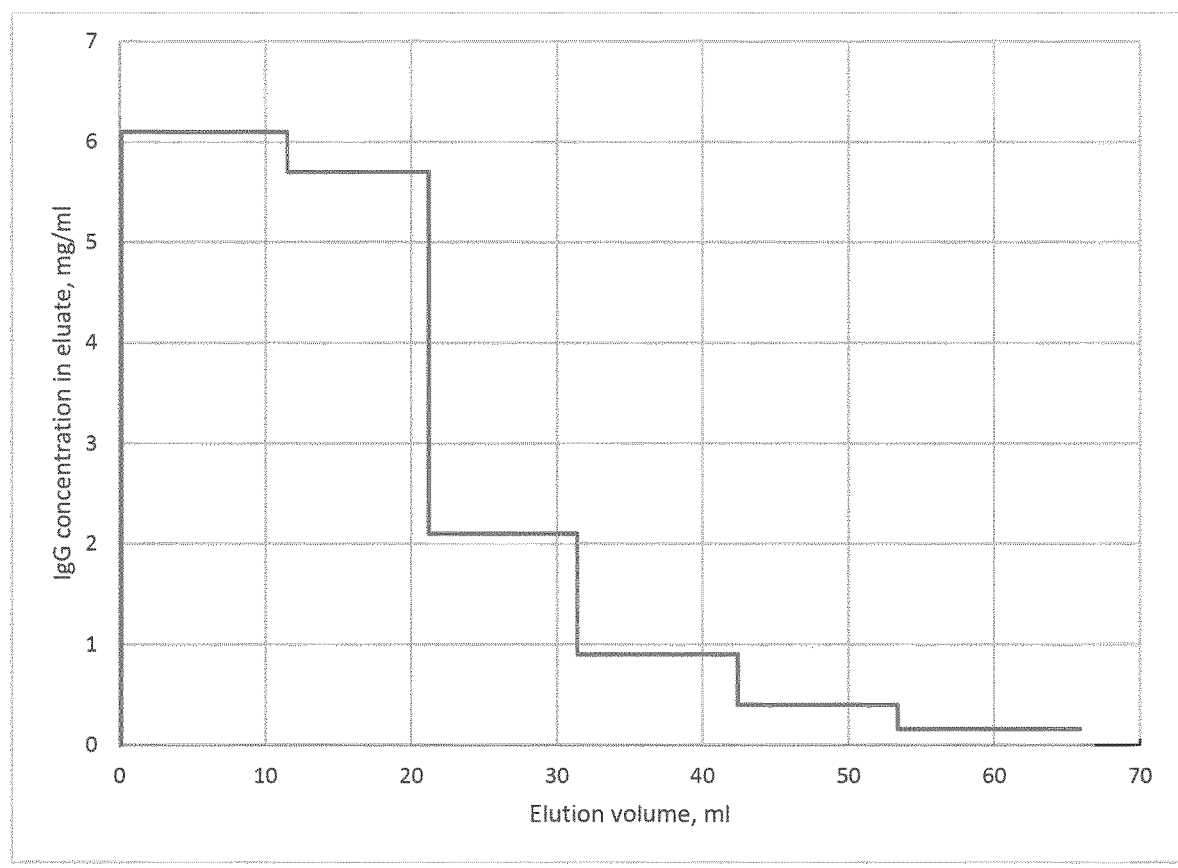
FIG. 8 shows an elution profile for the purification of IgG antibodies with magnetic beads using combinatory magnetic separation and filtration.

The concentration of IgG antibodies in the 6× elution fractions was determined spectrophotometrically at 280 nm using the absorbance of 1.38 at 1 mg/ml. Data is presented in Table 1 and FIG. 8. As presented, 90% of the eluted IgG antibodies was found in the 3 first elution fractions which corresponds to an elution volume of 3 column volumes.

TABLE 1

The amount IgG antibodies found in the 6× elution fractions.

| Elution no. | Eluted IgG, mg | Eluted IgG/total eluted IgG, % |
|---|---|---|
| 1 | 70 | 43 |
| 2 | 55 | 34 |
| 3 | 21 | 13 |
| 4 | 9.6 | 6 |
| 5 | 3.9 | 2 |
| 6 | 1.9 | 1 |
| Total | 161.4 | |

The invention claimed is:

1. A system for the separation of molecules in a mixture, said system comprises:
  a. a volume of magnetic beads,
  b. at least one first compartment adapted to receive said mixture, and said first compartment is adapted to handle said mixture together with the volume of magnetic beads having an affinity for at least one type of molecules to be separated,
  c. at least one magnet adapted to attract said volume of magnetic beads at least after contact of said mixture with said volume of magnetic beads, said at least one magnet is adapted to exert a magnetic field in at least a part of said first compartment,
  d. at least one second compartment, said at least one second compartment is adapted to receive said volume of magnetic beads after said magnetic beads have been at least partially collected with said at least one magnet,
  said system is adapted for transfer of said volume of magnetic beads from said at least one first compartment to said at least one second compartment with a flow of liquid, said at least one second compartment has a volume adapted to receive the volume of said magnetic beads, said at least one second compartment is adapted to elute said at least one type of molecules to be separated from said magnetic beads, said at least one second compartment has an outlet comprising means for retaining said magnetic beads in the at least one second compartment, the volume of the at least one second compartment is less than three times the volume of the magnetic beads.

2. The system according to claim 1, wherein said at least one magnet is at least one selected from the group consisting of a permanent magnet, and an electromagnet.

3. The system according to claim 1, wherein said at least one magnet can be inserted and retracted inside at least one sheath in the first compartment.

4. The system according to claim 1, wherein the first compartment comprises at least one nozzle adapted for directing a liquid at least partially towards a position where magnetic beads gather after being attracted by said at least one magnet.

5. The system according to claim 3, wherein at least one nozzle is adapted for directing a liquid at least partially towards the outside of said at least one sheath.

6. The system according to claim 1, wherein the system comprises pump(s) exerting low shear force on a pumped liquid.

7. The system according to claim 1, wherein the system comprises a peristaltic pump(s).

8. The system according to claim 1, wherein said system is adapted for handling cells.

9. The system according to claim 1, wherein the system is connected to a process computer system.

10. The system according to claim 1, wherein at least one from analogue and digital sensors are connected to a process computer system.

11. The system according to claim 1, wherein said system comprises at least one level sensor.

12. The system according to claim 1, wherein an UV-detector is at the outlet of said at least one second compartment.

13. The system according to claim 1, wherein a detector capable of measuring the optical density of a fluid is in said at least one first compartment.

14. The system according to claim 13, wherein said detector measures the optical density using light with a wavelength in the interval 400-600 nm.

15. The system according to claim 1, wherein the means for retaining said magnetic beads in the at least one second compartment is at least one selected from the group consisting of a net and a filter and which has a size of through pores so that the means for retaining said magnetic beads in the at least one second compartment has the ability of retaining the magnetic beads in the second compartment.

16. The system according to claim 1, wherein a sterile filter is at the outlet of the second compartment.

17. The system according to claim 1, wherein the second compartment is a storage for magnetic beads, when the system is not in use.

18. The system according to claim 1, wherein the second compartment is detachable and sealable.

19. The system according to claim 1, wherein parts of the system intended to be in contact with the mixture are intended for single use to be discarded after use and where other parts of the system are intended for use more than once.

20. The system according to claim 1, wherein the system is washable.

21. The system according to claim 1, wherein the system is autoclavable.

22. The system according to claim 1, wherein the system meets pharma engineering standards.

23. The system according to claim 1, wherein the at least one first compartment includes at least two first compartments in series.

24. The system according to claim 1, wherein the at least one first compartment includes at least two first compartments in parallel.

25. The system according to claim 1, wherein the at least one second compartment includes at least two second compartments in parallel.

26. The system according to claim 1, wherein the system comprises at least one second magnet adapted to attract said magnetic beads by exerting a magnetic field in at least a part of said second compartment.

* * * * *